United States Patent [19]

Gander et al.

[11] 4,190,594
[45] Feb. 26, 1980

[54] RETINOIC ACID DERIVATIVES

[75] Inventors: Robert J. Gander, Whitehouse; John A. Gurney, East Brunswick, both of N.J.

[73] Assignee: Johnson & Johnson, New Brunswick, N.J.

[21] Appl. No.: 906,168

[22] Filed: May 15, 1978

Related U.S. Application Data

[62] Division of Ser. No. 628,177, Nov. 3, 1975, Pat. No. 4,108,880.

[51] Int. Cl.$^2$ .................... C09F 5/00; C11C 3/00; A61K 7/42
[52] U.S. Cl. .................... 260/404; 260/404.5; 260/408; 260/410; 260/410.5; 260/410.6; 424/59; 424/305; 424/307; 542/418; 542/421; 542/429; 542/426
[58] Field of Search ......... 260/404, 404.5 R, 404.5 H, 260/408, 410 R, 410.5, 410.6; 424/59; 542/418, 421, 429, 426

[56] References Cited

U.S. PATENT DOCUMENTS

| 3,006,939 | 10/1961 | Pommer et al. | 260/410.9 V |
|---|---|---|---|
| 3,729,568 | 4/1973 | Kligman | 424/318 |
| 3,920,834 | 11/1975 | Klani et al. | 424/59 |
| 3,931,257 | 1/1976 | Pawson | 260/410.9 V |
| 3,950,418 | 4/1976 | Bollag et al. | 260/557 R |

*Primary Examiner*—John Niebling
*Attorney, Agent, or Firm*—Irving Newman

[57] ABSTRACT

Esters and amides of all-trans-retinoic acid are disclosed which are useful for their ultraviolet (UV) absorption properties.

8 Claims, No Drawings

RETINOIC ACID DERIVATIVES

This application is a division of copending application Ser. No. 628,177, filed Nov. 3, 1975, now U.S. Pat. No. 4,108,880 issued Aug. 22, 1978.

BACKGROUND OF THE INVENTION

Retinoic acid is known to be useful for the treatment of acne. See, for example, U.S. Pat. No. 3,729,568, which discloses the use of retinoic acid compositions for the treatment of acne. While retinoic acid is also known to have ultraviolet (UV) absorption properties, it is not useful as a sunscreen agent for skin application because of its irritating effects on human skin in effective sunscreening amounts, as well as other metabolic effects. Although these effects are useful in the treatment of acne, they negate the usefulness of retinoic acid as a human sunscreening agent. Surprisingly, of the forty-eight novel esters and amides of all-trans-retinoic acid which we have prepared, forty-one have been found to be non-irritating to human skin and to be substantially free of the metabolic effects characteristic of retinoic acid. The other seven compounds, which are useful for the treatment of acne, are the subject of our United States Patent 4,055,659 entitled "Retinoic Acid Derivatives."

SUMMARY OF THE INVENTION

This invention relates to novel esters and amides of all-trans-retinoic acid which are non-irritating to human skin and are substantially free of the metabolic effects characteristic of retinoic acid. More particularly, the present invention relates to:

(A) novel esters of all-trans-retinoic acid having the following formula:

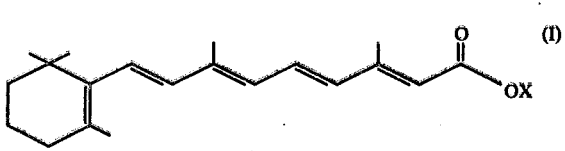

wherein X is a member selected from the group consisting of:

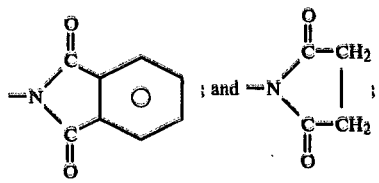

2-cyclohexylethyl; 10-carbomethoxydecyl; 4-hydroxybutyl; cholesteryl; mixed m- and p-vinylbenzyl; and 4-bromobenzyl;

(B) novel esters of all-trans-retinoic acid having the following formula:

wherein Y is a member selected from the group consisting of: cholesteryloxy; phenyl; 4-bromophenyl; 4-methoxyphenyl; 4-nitrophenyl; 4-hydroxyphenyl; 4-methylphenyl; 4-cyanophenyl; 4-ethoxyphenyl; 4-acetoxyphenyl; 2-naphthyl; 4-biphenyl; 2,5-dimethoxyphenyl; 2,4-dichlorophenyl; 2,4-dimethylphenyl; 3,4-diacetoxyphenyl; 3,4,5-trimethoxyphenyl; and 2,4,6-trimethylphenyl; and (C) novel amides of all-trans-retinoic acid having the following formula:

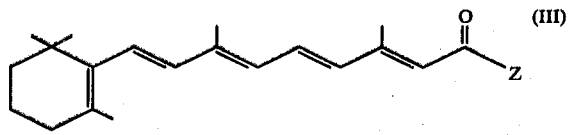

wherein Z is a member selected from the group consisting of: n-propylamino; tert-butylamino; 1,1,3,3-tetramethylbutylamino; 1-morpholino; 4-hydroxyphenylamino; 4-carbomethoxy-2-hydroxyphenylamino; β-(3,4-dimethoxyphenyl)-ethylamino; 2-benzothiazolylamino; 1-imidazolyl; 1-(2-nicotinoylhydrazolyl):

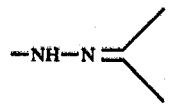

1-benzotriazolyl; 1-(1,2,4-triazolyl);

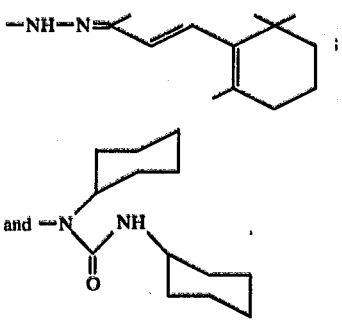

It has surprisingly been discovered that the retinoic acid derivatives of the invention, while possessing very good ultraviolet light absorption properties, do not have irritating effects on the skin and are substantially free of the metabolic effects which are characteristic of retinoic acid and, therefore, are useful as human sunscreen agents. That the compounds of the invention are substantially free of the metabolic effects characteristics of retinoic acid is demonstrated by their inactivity in the following test measuring DNA synthesis in which retinoic acid is significantly active at greater than 95% confidence level. Further, the present compounds generally do not produce the excessive erythema characteristic of retinoic acid.

Ten male guinea pigs (Hartley strain) weighing ca. 400 g. each were used for each compound to be tested. The animals were housed singly in wire cages, handled daily during experimentation, provided chow and water ad libitum, and maintained on 12/12 hour light/dark cycles. Prior to the experimental procedure, the animals were maintained as just described for three days.

On the first day of the test, one ear (dorsal skin) of each animal was randomly selected and treated with 0.025 ml. of the experimental solution, and the other ear was treated with an equal volume of the placebo vehicle (control). Ten animals for each compound were so treated. These topical applications were made at 9:00 a.m. on the first 4 days of the experiment. All the animals received chronic administration of tritiated thymidine ($^3$H-TdR) for these first four days. The $^3$H-TdR was given intraperitoneally at about 9:30 a.m., 1:30 p.m., and 5:00 p.m. of each day (10 micro Curie in 0.1 ml. $H_2O$/injection; specific activity=2.0 Curie/millimole). On the fifth day (9:00 a.m.), the animals were killed, and 6 mm. diameter punches of ear skin from the central portion of the treated sites were harvested.

Each of these tissue samples was solubilized at 37°–50° C. for 13 days in 1 ml. of an alkali solubilizer sold by Amersham-Searle Co. under the registered trademark "NCS" Solubilizer. The dissolved tissues kept in nylon scintillation vials were acidified with 0.025–0.050 ml. of acetic acid, and diphenyloxazole in toluene was added as a flour to detect the beta particles emitted by absorbed tritiated thymidine. The radioactivity of the samples was determined by multiple counting on a Beckman LS Counter. All count per minute values were quench corrected by external standardization to yield disintegrations per minute (dpm)/6 mm. punch of skin. Quench correction is especially important as some of the samples show faint yellow coloration due to presence of the retinyl derivatives, and therefore present considerable color quench.

The test compounds were found to be inactive (confidence level less than 90%) in the above test at up to 0.2% concentration by weight when applied in 50:50 parts by weight propylene glycol-ethanol or 35:35:30 parts by weight propylene glycol-ethanol-chloroform.

The subject compounds strongly absorb ultraviolet (UV) light, generally above 280 nm., and are useful as UV-screening materials, for example, in plastic products and sunburn preventive formulations. They may be used as UV-absorbers in plastics and resins such as, for example, polystyrene, polyethylene, polypropylene, polyacrylics (e.g., methacrylate resins, polyacrylamides, polyacrylonitrile fibers, etc.), polyamide (e.g., nylon) fibers, and polyester fibers. The inclusion of about 0.01–5.0 percent of the absorber, based on the polymer weight, is usually sufficient to render protection against UV light, such as in plastic films, light filters, etc. The absorber may be incorporated into the mixture of monomers before polymerization to form the polymer or it may be incorporated into the polymer at other stages during its handling, as by milling into the polymer together with other compounding ingredients, or during the spinning of the polymer into fibers, etc. The compounds are preferably employed as sunscreening agents in typical anti-sunburn formulations in amounts of about 0.5–10 percent by weight (see G. W. van Ham & W. P. Herzog, Chapter 6, "The Design of Sunscreen Preparations," in "Drug Design IV," E. J. Ariens, Ed., Academic Press, N.Y. and London 1973).

The compounds of the invention may be prepared by one of the following methods:

(A) In the first method of preparation, all-trans-retinoic acid or an alkali metal salt of all-trans-retinoic acid is reacted with an appropriate alkyl halide. This reaction is conducted in an appropriate inert organic solvent, such as for example an ether (e.g., diethylether, tetrahydrofuran, and the like), an ester such as ethyl acetate, or the like. The desired product may be isolated and purified by methods known in the art.

(B) In the second method, all-trans-retinoyl chloride is reacted with an appropriate amine or alcohol to form the desired ester or amide. The alcohol or amine is preferably present in a slight molar excess, and the reaction may be conducted in an appropriate inert organic solvent such as for example an aromatic hydrocarbon (e.g., benzene, toluene, xylene, and the like), a halogenated hydrocarbon (e.g., chloroform, carbon tetrachloride and the like), and the like.

(C) The hydrazone compounds of the invention are prepared by refluxing all-trans-retinoyl hydrazide with the appropriate ketone in a lower alkanol solution. The solution preferably also can contain a trace of pyridine.

(D) The imide compounds of the invention may be prepared by reacting all-trans-retinoyl chloride with the appropriate N-hydroxyimide in an appropriate inert organic solvent such as for example an aromatic hydrocarbon (e.g., benzene, toluene, xylene, or the like), a tertiary amide such as N,N-dimethylformamide, and the like.

The desired products may be isolated and purified by methods known in the art. The preparation of the compounds of this invention is illustrated by the following examples.

EXAMPLE I

10-Carbomethoxydecyl all-trans-Retinoate

The following were stirred together at 65° C. in a nitrogen atmosphere for 24 hours: powdered potassium all-trans-retinoate (3.38 g.; 0.010 mole); powdered potassium iodide (1.66 g.; 0.010 mole); methyl 11-bromoundecanoate (4.20 g.; 0.0150 mole); dry tetrahydrofuran, 30 ml. The reaction mixture was filtered with suction through sintered glass, and the filtrate was evaporated to give a thick red liquid. The liquid was dissolved in 100 ml. of 95:5 petroleum ether-benzene and put on a chromatographic column of 40–140 mesh silica gel. The column was eluted with 50:50 petroleum ether-benzene. Fractions containing a mixture of retinoate ester and unreacted bromoester were collected and evaporated to give a yellow oil from which the retinoate crystallized when cooled and seeded. The crude crystals were suction filtered from unreacted bromoester. One recrystallization from 12.5 ml. of methanol yielded the retinoate ester, melting point 53°–55° C.; which showed the correct proton magnetic resonance spectrum and elemental analysis. Anal. Calcd. for $C_{32}H_{50}O_4$: C, 77.1; H, 10.1. Found: C, 76.7; H, 10.1.

EXAMPLE II

Cholesteryl all-trans-Retinoate

A solution of retinoyl chloride was prepared from 3.0 g of all-trans-retinoic acid and 0.92 g. of phosphorous trichloride in 20 ml. of benzene. This solution was added during 18 minutes to 3.48 g. of cholesterol and 28 ml. of N,N-dimethylaniline with stirring and heating to 90° C. in an open-neck flask. Stirring was continued for an additional 40 minutes, during which most of the benzene evaporated. The reaction mix was dissolved in 300 ml. of ethyl ether, and the ether solution was successively extracted with three 50-ml. portions of cold 2 N sulfuric acid, two 50-ml. portions of cold saturated sodium bicarbonate solution, and four 50-ml. portions of cold water. Crystals formed in the ether solution as it stood in the refrigerator overnight. They were twice recrystallized from 50:50 chloroform-ethanol (20 ml. per gram), giving pure product, melting point 162°–163°

C. The proton magnetic resonance spectrum was consistent with the structure. Anal. Calcd. for $C_{47}H_{72}O_2$: C, 84.4; H, 10.8. Found: C, 84.5; H, 10.8.

EXAMPLE III

N,N'-Dicyclohexyl-N-(all trans-Retinoyl)-Urea

The following were magnetically stirred in a 50-ml. flask at room temperature for 48 hours: 3.00 g. of all-trans-retinoic acid, 2.06 g. of N,N'-dicyclohexylcarbodiimide, 1.01 g. of triethylamine, 15 ml. of dry tetrahydrofuran. The solid in the reaction mixture was filtered off and washed with 20 ml. of tetrahydrofuran. Evaporation of the tetrahydrofuran filtrate plus washings left a yellow, pasty solid which was then diluted with 150 ml. of ethyl ether. The ether was washed with 25 ml. of cold 5% hydrochloric acid, with 25 ml. of cold saturated potassium bicarbonate, and finally with four successive 25-ml. portions of ice water. During the washing procedure, a finely-divided solid separated from the ether. It was crystallized from 112 ml. of acetone. The crystals melted at 171°–172° C. The proton magnetic resonance spectrum confirmed the structure of the compound. Anal. Calcd. for $C_{33}H_{50}N_2O_2$: C, 78.2; H, 9.94; N, 5.53. Found: C, 78.2; H, 10.2; N, 5.43.

EXAMPLE IV

Trans-$\beta$-Ionone (All-trans-Retinoyl)-Hydrazone

A solution of retinoyl chloride was prepared from 3.0 g. of all-trans-retinoic acid and 0.92 g. of phosphorous trichloride in 50 ml. of benzene by stirring at room temperature for 2.2 hours. This solution was added dropwise to a stirred solution of 4.80 g. of dry hydrazine in 20 ml. of anhydrous ethyl ether during 30 minutes while cooling in an ice bath. Stirring was continued for three hours at room temperature, then for an additional hour at 50°–60° C. The reaction mixture was diluted with 150 ml. of ethyl ether, then extracted with four 25-ml. portions of ice water. After drying over sodium sulfate, the ether solution was evaporated leaving crude all-trans-retinoyl hydrazide.

The hydrazide was dissolved in 15 ml. of 95% ethanol, and to the solution was added 7.68 g. of trans-$\beta$-ionone in 15 ml. of 95% ethanol and one drop of pyridine. The solution was refluxed for 15 minutes, filtered, and cooled in ice, causing precipitation of yellow crystals. These crystals were recrystallized from 1:8 chloroform-ethanol (22.5 ml. per gram), giving pure product, melting point 183°–185° C., which exhibited the correct proton magnetic resonance spectrum. Anal. Calcd. for $C_{33}H_{48}N_2O$: C, 81.1; H, 9.90; N, 5.73. Found: C, 81.1; H, 10.0; N, 5.51.

EXAMPLE V

N-(All-trans-Retinoyloxy)-Succinimide

A solution of retinoyl chloride was prepared by magnetically stirring 3.00 g. of all-trans-retinoic acid and 0.92 g. of phosphorous trichloride for two hours in 50 ml. of dry benzene at room temperature. This solution was added dropwise during 30 minutes at room temperature to a stirred solution of 5.75 g. of N-hydroxysuccinimide dissolved in 10 ml. of dry, N,N-dimethylformamide. The reaction mixture was stirred for 1.5 hours longer, then immersed in an 80° C. oil bath for 15 minutes. The reaction mixture was diluted with 150 ml. ethyl ether, and the thick red oil which did not dissolve was discarded. The ether solution was washed with five 30-ml. portions of ice water and dried over sodium sulfate. Evaporation of the solvents left a yellow powder which was recrystallized twice from 1:2 chloroform-n-hexane (7.5 ml. per gram) and once from isopropanol (25 ml. per gram). Product melting point was 177°–179° C. The proton magnetic resonance spectrum was consistent with the structure. Anal. Calcd. for $C_{24}H_{31}NO_4$: C, 72.5; H, 7.86; N, 3.52. Found: C, 72.5; H, 7.91; N, 3.50.

EXAMPLE VI

2-Cyclohexylethyl all-trans-Retinoate

The following were refluxed in an aluminum foil-covered flask under nitrogen for 28 hours: 5.0 g. of all-trans-retinoic acid; 3.5 g. of cyclohexylethyl bromide; 15.0 g. of anhydrous potassium carbonate; 0.05 g. of potassium iodide; 0.05 g. of p-methoxyphenol; and 50 ml. of tetrahydrofuran. The reaction mixture was then diluted with 200 ml. of n-hexane and filtered through a one-half-inch-thick pad of alumina. The pad was eluted with 100 ml. of 1:1 benzene-n-hexane and the washings were combined with the original filtrate. The solvents were removed on a rotary evaporater, and the residual yellow oil was placed on a silica gel column (100 g.) with 20 ml. of n-hexane. The column was eluted with 600 ml. of 1:1 benzene-n-hexane. The first 200 ml. of eluted solution were discarded; the next 300 ml. were collected, and the solvent was evaporated. The yellow oil residue was evacuated for two days at a pressure of 0.03 mm. and room temperature. The proton magnetic resonance spectrum of the resulting oil was consistent with the structure. Anal. Calcd. for $C_{28}H_{42}O_2$: C, 81.9; H, 10.3. Found: C, 81.8; H, 10.3.

EXAMPLE VII

4-Hydroxybutyl all-trans-Retinoate

A solution of retinoyl chloride was prepared by stirring 3.0 g. of all-trans-acid and 0.92 g. of phosphorous trichloride in 25 ml. of dry benzene for about two hours. A solution of 6.0 ml. of 1,4-butanediol and 8.0 ml. of pyridine was stirred magnetically, cooled to 4° C., and the retinoyl chloride solution was added during five minutes. The reaction mixture was stirred at 20° C. for 50 minutes, and then at 43° C. for 15 minutes, all under a nitrogen atmosphere. The lightamber reaction mixture was diluted with 20 ml. of ethyl ether. The resulting solution was washed with two 20-ml. portions of 5 percent hydrochloric acid, 20 ml. of cold 10 percent sodium bicarbonate solution, and 20 ml. of cold brine solution. The washed ether solution was then dried over magnesium sulfate.

The washed and dried solution was placed on 80 ml. of alumina and eluted successively with 200 ml. of ethyl ether and 600 ml. of ethyl acetate. Crude product was concentrated from the ethyl acetate eluate and again placed on alumina (75 ml.) with the aid of 20 ml. of ethyl ether. The product was eluted from the alumina with 1,400 ml. of ethyl ether. Composition of the fractions was monitored by thinlayer chromatography. The appropriate fractions were combined, the ether evaporated, and the residual viscous yellow oil was evacuated at a pressure of 0.005 mm. for 24 hours. The proton magnetic resonance spectrum of the product was consistent with the structure. Anal. Calcd. for $C_{24}H_{36}O_3$: C, 77.4; H, 9.74. Found: C, 77.4; H, 9.96.

EXAMPLE VIII

All-trans-Retinoyloxyacetyl-3,4,5-Trimethoxybenzene:

Potassium retinoate was made by neutralizing 3.00 g. of all-trans-retinoic acid in 30 ml. of tetrahydrofuran with 15.6 ml. of 0.640 N methanolic potassium hydroxide. The solvent was evaporated in a rotary evaporator, and the residue was dried at a pressure of less than 0.5 mm. for several hours.

Powdered potassium retinoate (3.03 g.) in 20 ml. of hexamethylphosphoramide was stirred overnight at room temperature with 2.89 g. of 2-bromo-3',4',5'-trimethoxyacetophenone. The turbid yellow reaction mixture was poured into 30 ml. of cold 5% hydrochloric acid, precipitating a sticky yellow solid. The solid hardened when washed by decantation with 60 ml. of cold water. The solid was dissolved in 200 ml. ethyl ether, and the ether solution was washed with five 25-ml. portions of cold water. After drying over sodium sulfate, the ether solution was evaporated leaving a yellow powder.

The powder was recrystallized twice from 1:2 chloroform-methanol (7.5 ml. per gram), giving yellow crystals, melting point 123.0°–123.5° C. The proton magnetic resonance spectrum of the product was consistent with the structure. Anal. Calcd. for $C_{31}H_{40}O_6$: C, 73.2; H, 7.93. Found: C, 73.3; H, 7.93.

EXAMPLE IX 4-(All-trans-Retinoyl)-Aminophenol

A solution of retinoyl chloride was prepared by magnetically stirring 3.00 g. of all-trans-retinoic acid and 0.92 g. of phosphorous trichloride for 2.25 hours in 50 ml. of dry benzene. During 21 minutes, the retinoyl chloride solution was then added to a solution of 5.46 g. of 4-aminophenol in 16 ml. of anhydrous N,N-dimethylformamide and 2 ml. of anhydrous ethyl ether, while stirring under a nitrogen atmosphere and cooling in an ice bath. Stirring was then continued for three hours at room temperature and for an hour more at 50° C.

The reaction mixture was diluted with 150 ml. of ethyl ether. The ether solution was extracted with two 25-ml. portions of cold 5% hydrochloric acid and then was washed with four 25-ml. portions of cold water. After the washed solution was dried over sodium sulfate, the solvent was evaporated, leaving a dark-yellow solid. The solid was recrystallized first from methanol (6 ml. per gram), then from 1:1.7 chloroform-n-hexane (8 ml. per gram). The product had a melting point of 159°–160° C. The proton magnetic resonance spectrum of the product was consistent with the structure with no extraneous resonances. Anal. Calcd. for $C_{26}H_{33}NO_2$: C, 79.8; H, 8.49; N, 3.58. Found: C, 79.5; H, 8.67; N, 3.56.

EXAMPLE X

Following the method of Example IV, but substituting an equivalent amount of acetone for the trans-$\beta$-ionone used therein, there is prepared acetone (all-trans-retinoyl)hydrazone; m.p. 174°–175° C.

EXAMPLE XI

Following the method of Example V, but substituting an equivalent amount of N-hydroxyphthalimide for the N-hydroxysuccinimide used therein, there is prepared N-(all-trans-retinoyloxy)-phthalimide; m.p. 177°–178° C.

EXAMPLE XII

Following the method of Example VIII, but substituting an equivalent amount of the appropriate halogen-containing compound for the 2-bromo-3',4',5'-trimethoxyacetophenone used therein, the following are prepared:

| Compound | m.p. (°C.) |
|---|---|
| Cholesteryl all-trans-Retinoyloxyacetate | 104–106 |
| Mixed m- and p-vinylbenzyl all-trans-Retinoates | Liquid |
| 4-Bromobenzyl all-trans-Retinoate | 70.0–70.5 |
| all-trans-Retinoyloxyacetylbenzene | 132–133 |
| 4-(all-trans-Retinoyloxyacetyl)-bromobenzene | 136–137 |
| 4-(all-trans-Retinoyloxyacetyl)-methoxybenzene | 126–127 |
| 4-(all-trans-Retinoyloxyacetyl)-nitrobenzene | 151–152 |
| 4-(all-trans-Retinoyloxyacetyl)-phenol | 180–181 |
| 4-(all-trans-Retinoyloxyacetyl)-toluene | 125–126 |
| 4-(all-trans-Retinoyloxyacetyl)-benzonitrile | 178–179 |
| 4-(all-trans-Retinoyloxyacetyl)-ethoxybenzene | 124.5–125.5 |
| 4-(all-trans-Retinoyloxyacetyl)-acetoxybenzene | 132—133 |
| 2-(all-trans-Retinoyloxyacetyl)-naphthalene | 120–121 |
| 4-(all-trans-Retinoyloxyacetyl)-biphenyl | 142–143 |
| all-trans-Retinoyloxyacetyl-2,5-dimethoxybenzene | 98–99 |
| all-trans-Retinoyloxyacetyl-2,4-dichlorobenzene | 1:06–107 |
| all-trans-Retinoyloxyacetyl-2,4-dimethylbenzene | 117.5–1118.5 |
| all-trans-Retinoyloxyacetyl-3,4-diacetoxybenzene | -diacetoxy- 123—124 |
| all-trans-Retinoyloxyacetyl-2,4,6-trimethylbenzene | 116–117 |

EXAMPLE XIII

Following the method of Example IX, but substituting an equivalent amount of the appropriate amine for the 4-aminophenol used therein, the following are prepared:

| Compound | m.p. (°C.) |
|---|---|
| N-n-Propyl all-trans-retinamide | 113–115 |
| N-Tert.-butyl all-trans-retinamide | 139–141 |
| N-(1,1,3,3-Tetramethyl)-butyl all-trans-retinamide | Glass |
| N-(all-trans-Retinoyl)-morpholine | 82–84 |
| Methyl 4-(all-trans-Retinoylamino)-salicylate | 198–199 |
| N-(all-trans-Retinoyl)-imidazole | 113–115 |
| 1-Nicotinoyl-2-(all-trans-retinoyl)-hydrazine | 191–194 |
| 1-(all-trans-Retinoyl)-benzotriazole | 140–141 |
| 1-(all-trans-Retinoyl)-1,2,4-triazole | 141–142 |
| N-[$\beta$-(3,4-Dimethoxyphenyl)ethyl]-all-trans-retinamide | 140–142 |
| 2-(all-trans-Retinoylamino)-benzothiazole | 219–221 |

The use of the compounds of the invention is illustrated by the following example. All parts are by weight.

EXAMPLE XIV

The following ingredients are homogeneously mixed to produce a formulation useful as a human sunscreening cream for topical application to the skin:

| Ingredient | Parts |
| --- | --- |
| Glyceryl Stearate | 10.0 |
| Isopropyl Myristate | 10.0 |
| Spermaceti | 5.0 |
| Cetyl Alcohol | 2.5 |
| Steareth-20 | 2.625 |
| Steareth-2 | 0.375 |
| Propylene Glycol | 5.0 |
| Xanthan Gum | 0.3 |
| Sorbic Acid | 0.2 |
| Butylated Hydroxytoluene | 0.05 |
| Active Ingredient | 2.5 |
| Water | 61.45 |

The active ingredient is any of the compounds of the present invention.

What is claimed is:

1. A derivative of all-trans-retinoic acid selected from the group consisting of:

(A) esters of all-trans-retinoic acid having the following formula:

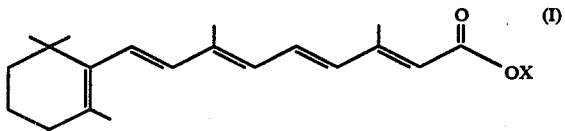

wherein X is a member selected from the group consisting of: 2-cyclohexylethyl; 10-carbomethoxydecyl; 4-hydroxybutyl; cholesteryl; 4-bromobenzyl;

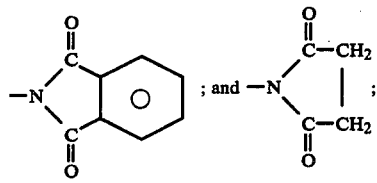

(B) esters of all-trans-retinoic acid having the following formula:

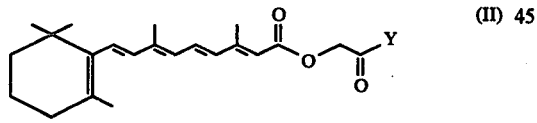

wherein Y is a member selected from the group consisting of: cholesteryl; phenyl; 4-bromophenyl; 4-nitrophenyl; 4-cyanophenyl; and 2,4-dichlorophenyl; and (C) amides of all-trans-retinoic acid having the following formula:

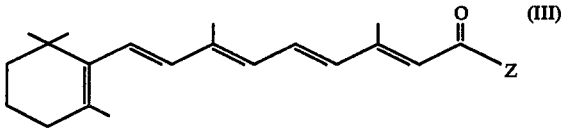

wherein Z is a member selected from the group consisting of: n-propylamino; tert.-butylamino; 1,1,3,3-tetramethylbutylamino; 4-hydroxyphenylamino; 4-carbomethoxy-3-hydroxyphenylamino; β-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl);

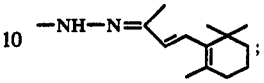

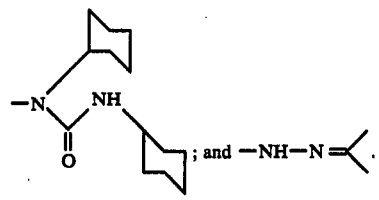

2. An amide of all-trans retinoic acid according to claim 1 having the following formula:

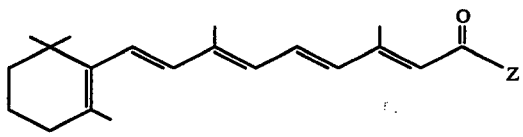

wherein Z is a member selected from the group consisting of: n-propylamino; tert.-butylamino; 1,1,3,3-tetramethylbutylamino; 4-hydroxyphenylamino; 4-carbomethoxy-3-hydroxyphenylamino; β-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl);

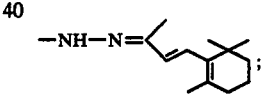

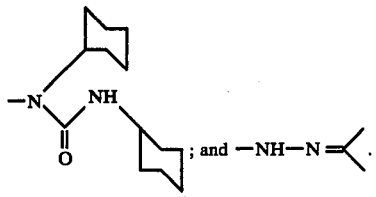

3. N-n-Propyl all-trans-retinamide according to claim 2.

4. N-Tert.-butyl all-trans-retinamide according to claim 2.

5. N-(1,1,3,3-Tetramethyl)-butyl all-trans-retinamide according to claim 2.

6. N-[β-(3,4-Dimethoxyphenyl)ethyl]-all-trans-retinamide according to claim 2.

7. N-(4-hydroxyphenyl)-all-trans-retinamide according to claim 2.

8. N-(4-carbomethoxy-3-hydroxyphenyl)-all-trans retinamide according to claim 2.

* * * * *